(12) United States Patent
Ciezki et al.

(10) Patent No.: US 6,309,339 B1
(45) Date of Patent: *Oct. 30, 2001

(54) INTRAVASCULAR RADIATION DELIVERY DEVICE

(75) Inventors: Jay P Ciezki, Shaker Heights, OH (US); Eugene J. Jung, Jr., San Diego, CA (US); Eric J. Lee, Pepper Pike; Emin M. Tuzcu, Pepperpike, both of OH (US); James D. Savage, Escondido, CA (US); Martin S. Weinhous, Moreland Hills, OH (US)

(73) Assignee: Endosonics Corporation, Rancho Cordova, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/118,308

(22) Filed: Jul. 16, 1998

Related U.S. Application Data

(63) Continuation-in-part of application No. 08/827,489, filed on Mar. 28, 1997, now Pat. No. 6,033,357.

(51) Int. Cl.⁷ .............................. A61M 29/02; A61N 5/60
(52) U.S. Cl. ...................................................... 600/3
(58) Field of Search ................................. 600/1–8, 924, 600/427

(56) References Cited

U.S. PATENT DOCUMENTS

| 4,799,479 | 1/1989 | Spears . |
| 5,019,075 | 5/1991 | Spears et al. . |
| 5,053,033 | 10/1991 | Clarke . |

(List continued on next page.)

FOREIGN PATENT DOCUMENTS

| 9102312 | 8/1992 | (DE) . |
| 0867200A2 | 9/1998 | (EP) . |
| 96/10436 | 4/1996 | (WO) . |
| WO 97/18012 | 5/1997 | (WO) . |
| WO 99/11325 | 3/1999 | (WO) . |

OTHER PUBLICATIONS

Mayberg et al., "Radiation Inhibition of Intimal Hyperplasia after Arterial Injury", *Radiation Research*, No. 142, pp. 212–220 (1995).

Popowski, et al, "High Dose Rate Brachytherapy for Prevention of Restenosis after Percutaneous Transluminal Coronary Angioplasty: Preliminary Dosimetric Tests of a New Source Presentation", Int. J. Radiation Oncology Biol. Phys., vol. 33, No. 1, pp. 211–215 (1995).

Shimotakahara, et al, "Gamma Irradiation Inhibits Neoimtimal Hyperplasia in Rats After Arterial Injury", Department of Otolaryngology Head and neck Surgery (S.S.) and Neurological Surgery (M.R.M.) University of Washington, Seattle VA Medical Center, Seattle, Wash., pp. 424–428, accepted Sep. 13, 1993 *Stroke*, vol. 25, No. 2, Feb. 1994.

(List continued on next page.)

*Primary Examiner*—Samuel G. Gilbert
(74) *Attorney, Agent, or Firm*—Nydegger & Associates

(57) ABSTRACT

A device and method for precisely delivering dosage of radiation from a radiation source to a treatment site of a vessel is provided herein. In one embodiment, the device includes a catheter which inserts into a vessel lumen of the body. The catheter includes an adjuster section for altering a portion of the radiation emitting radially from the radiation source so that the radiation source delivers an asymmetrical radiation profile to the vessel. The device can also include a catheter supporter which inhibits rotational deformation in the catheter between a catheter distal end and a catheter proximal end. This allows the delivery section to be precisely rotated to properly position the adjuster section within the vessel lumen.

28 Claims, 11 Drawing Sheets

U.S. PATENT DOCUMENTS

| | | |
|---|---|---|
| 5,199,939 | 4/1993 | Dake et al. . |
| 5,213,561 | 5/1993 | Weinstein et al. . |
| 5,283,257 | 2/1994 | Gregory et al. . |
| 5,302,168 | 4/1994 | Hess . |
| 5,304,115 | 4/1994 | Pflueger . |
| 5,344,402 | 9/1994 | Crocker . |
| 5,345,945 | 9/1994 | Hodgson et al. . |
| 5,354,257 | 10/1994 | Roubin et al. . |
| 5,358,959 | 10/1994 | Halperin et al. . |
| 5,377,682 | 1/1995 | Ueno . |
| 5,503,171 | 4/1996 | Weinberger . |
| 5,562,594 | 10/1996 | Weeks . |
| 5,569,220 | 10/1996 | Webster . |
| 5,611,812 | 3/1997 | Skornia . |
| 5,643,171 | 7/1997 | Bradshaw et al. . |
| 5,683,345 | 11/1997 | Waksman et al. . |
| 5,772,642 | 6/1998 | Ciamacco, Jr. . |
| 5,840,008 | 11/1998 | Klein et al. . |
| 5,846,204 | 12/1998 | Solomon . |
| 5,863,284 | 1/1999 | Klein . |
| 6,033,357 * | 3/2000 | Ciezki et al. .............................. 600/3 |
| 6,077,213 * | 6/2000 | Ciezki et al. .............................. 600/3 |

OTHER PUBLICATIONS

Waksman et al., "Intracoronary Low–Dose B–Irradiation Inhibits Neointima Formation After Coronary Artery Balloon Injury in the Swine Restenosis Model", From Andreas Gruentzig Cardiovascular center Division of cardiology, Department of Medicine (R.W., K.A.R., G.D.C., S.B.K.); Department of Radiation Oncology (I.R.C.); Department of Pathology, Emory University School of Medicine (M.B.G.); Health Physics program, Georgia Institute of Technology (C.W.); and Novoste Corporation (R.A.H.), Atlanta, Ga., pp. 3025–3031, accepted Jun. 13, 1995.

Wiedermann, et al, "Effects of High–Dose Intracoronary Irradiation on Vasomotor Function and Smooth Muscle Histopathology", *Intracoronary Irradiation and Vasomotion,* The American Physiology Society, pp. H125–H132, (1994) *Circulation,* Vo. 92, No. 10, Nov. 15, 1995.

Wiedermann, et al, "Intracoronary irradiation markedly Reduces Restenosis after Baloon Angioplasty in a Porcine Model", Departments of Medicine and Radiation Oncology, and Section of Presbyterian Medical Center and Columbia University, New York, New York, accepted Dec. 22, 1993. JACC, vol. 23, No. 6, May 1994, pp. 1491–1498.

Wiedermann, et al, "Intracoronary Irradiation markedly Reduces Neointimal Proliferation After Balloon Angioplasty in Swine: Persistent Benefit at 6–Month Follow–Up" *JACC,* vol. 25, No. 6, May 1995; pp. 1451–1456.

Popowski, et al, "Endovascular B–Irradiation after Percutaneous Transluminal Coronary Balloon Angioplasty", *Int. J. Radiation Oncology Bio. Phys.,* vol. 36, No. 4, pp. 841–845, (1996).

Schopohl, et al. "Ir Endovascular Brachytherapy for avoidance of Intimal Hyperplasia after percutaneous Transluminal Angioplasty and Stent Implantation in Peripheral Vessels: 6 Years of Experience" *Int. J. Radiation Oncology Bio. Phys.,* vol. 36, No. 4, pp. 835–840, (1996).

Marcial–Rojas–Castro, San Juan Puerto Rico, "Irradiation Injury to Elastic Arteries in the Course of Treatment for Neoplastic Disease," From the Department of Pathology of the University of Puerto Rico School of Medicine and the Dr. I. González Martinez Oncologic Hospital.

Sinzinger et al. "Enhanced Mitotic Activity Induced by Irradiation is Abolished by PG12 Pretreatment," *Prostaglandins,* Jan., 1991, vol. 41, No. 1., pp. 57–65.

Martin, et al., "Elastin Synthesis and Accumulation in Irradiated Smooth Muscle Cell Cultures," *Connective Tissue Research,* 1992, vol. 28, pp. 181–189.

Eldor, et al., "Perturbation of Endothelial Functions by Ionizing Irradiation: Effects of Prostaglandins, Chemoattractants and Mitogens," Seminars in Thrombosis and Hemostatis, vol. 15, No. 2, pp. 215–225, 1989.

Appplefeld, et al., "Cardiac Disease After Radiation Therapy for Hodgkin's Disease: Analysis of 48 Patient", The American Journal of Cardiology, pp 1679–1681, vol. 51, Jun., 1983.

Hicks, George L. M.D., "Coronary Artery Operation in Radiation–Associated Atherosclerosis: Long–Term Follow–up," *Ann Thorac, Surg,;* 53, pp. 670–674, (1992).

Fajardo, et al, "Morphology of Radiation–Induced Heart Disease", *Arch Path,* vol. 86, Nov. 1968, pp. 512–519.

Wilcox, et al, "The Role of the Adventitia in the Arterial Response to Angioplasty: The Effect of Intravascular Radiation", Int. J. Radiation Oncology Biol. Phys. vol. 36, No. 4, pp. 789–796, 1996.

Sinzinger, et al., "Morphologische und Zellkinetische Untersuchungen an der Arterienwand nach Rötgenbestrahlung. I. gebnisse bei 3000rad. Herdbestrahlungdosis am Kaninchen", *Acta Morpho. Nerl.–Scand* 14 (1976), pp. 201–214, Apr. 27, 1975.

Frank M. Waterman, Ph.D. & David E. Holcomb, Ph.D., Dose Distributions Produced by a Shielded Vaginal Cylinder Using a High–Activity Iridium–192 Source, Philadelphia, Pennsylvania. There is evidence that this document was available at least as early as Jan., 1995.

Nucletron® Corporation, Applicators catalog, Columbia, Maryland. The Applicants are unsure about the date of this publication. However, the number "92" is listed on the back cover, in the bottom right hand corner. Therefore, the catalog may have been published in 1992.

* cited by examiner

INTRAVASCULAR RADIATION DELIVERY DEVICE

This Application is a Continuation-In-Part of application Ser. No. 08/827,489, filed Mar. 28, 1997, now U.S. Pat. No. 6,033,357. The contents of application Ser. No. 08/827,489 are incorporated herein by reference.

FIELD OF THE INVENTION

The present invention relates generally to a device and method for treating a blockage or stenosis in a vessel of a patient. More specifically, the present invention relates to a device and method for precisely and accurately delivering a dosage of radiation to a vessel to inhibit re-stenosis.

BACKGROUND

It is well known that many medical complications are caused by a partial or total blockage or stenosis of a blood vessel in a patient. Depending on the location of the stenosis, the patient can experience cardiac arrest, stroke or necrosis of tissues or organs. Commonly, the stenosis is caused by the build-up of artherosclerotic plaque in the intima of the vessel. The plaque typically builds up irregularly in the vessel. As a result of the irregular build-up of plaque, the lumen of the vessel, in most blocked vessels, is not centrally located relative to the external elastic lamina.

Several procedures have been developed to treat stenoses, including angioplasty, stenting, and atherectomy. However, none of these procedures are entirely successful in inhibiting or preventing the re-stenosis of a vessel after the procedure is completed.

Recent studies have demonstrated that radiation may inhibit or prevent re-stenosis in the vessel by inhibiting or preventing the growth of fibrotic cells in the vessel wall, commonly referred to as neointima. The precise target for the radiation in the vessel is currently not known. However, it is believed that the adventitia may be a key source of growth of the neointima. Therefore, it is theorized that the entire vessel, including the adventitia should be treated with radiation.

At least one delivery device has been used for performing intravascular radiation treatment on a treatment site of the vessel. This delivery device utilizes a catheter to position a radiation source in the vessel lumen, adjacent the treatment site. The radiation source is positioned in the vessel lumen and is allowed to emit radiation until the prescribed dosage is released. With this delivery device, the tissue closest to the radiation source receives a larger radiation dosage than the tissue farthest from the radiation source. Subsequently, the radiation source is removed from the vessel lumen.

However, the results obtained using this type of delivery device are not entirely satisfactory. Specifically, because the growth of the plaque inside the vessel is irregular and/or the vessel is curved, the radioactive source is not centered in the vessel relative to the vessel lamina. Thus, depending upon the dosage prescribed, this can result in undertreating certain portions of the vessel and overtreating certain other portions of the vessel. For example, certain portions of the vessel lamina will receive a larger dosage of radiation than other portions of the vessel lamina.

Undertreating with radiation can result in not inhibiting the neointima and, in some instances, can actually result in stimulating smooth muscle cell proliferation and extracellular matrix production. Overtreating with radiation can, for example, induce necrosis or an aneurysm. Therefore, it is important to avoid overtreating and/or undertreating of a treatment site of the vessel.

One attempt to solve this problem involves accurately centering the delivery device in the vessel, relative to the vessel lumen. This can be accomplished using a variety of mechanical devices, such as a centering balloon or an expandable mechanical strut. However, these mechanical devices add excessive mass and bulk to the delivery device. This limits the usefulness of the present delivery device to relatively large vessels, i.e., three and one-half millimeters (3.5 mm) or larger and increases the risk of occluding blood flow in the vessel. Moreover, there is a risk that the delivery device will not be accurately centered.

In light of the above, it is an object of the present invention to provide a device and method for delivering a precise dose of radiation to a treatment site within a vessel without centering the delivery device. Another object of the present invention to provide a device and method for delivering a substantially uniform dose of radiation to the vessel lamina and other areas of the vessel. Another object of the present invention is to provide a device which can be used to precisely evaluate the amount and distribution of atherosclerotic plaque in a vessel and which can tailor the treatment in view of the evaluation. Still another object of the present invention is to provide a device and method which is relatively safe and easy to use in curved vessels. Another object of the present invention is to provide a device which can be easily adapted to meet the specific needs of the patient. Still another object of the present invention is to provide a device for accurately providing a treatment plan based upon the configuration of the treatment site of the vessel. Yet another object of the present invention is to provide a device which is relatively simple and inexpensive to manufacture.

SUMMARY

The present invention is directed to a device which satisfies these objectives. The device is useful for delivering an asymmetrical dose of radiation to a treatment site of a vessel to treat a stenosis in the vessel. In one embodiment, the device includes an adjuster section adapted to be positioned into the vessel. As provided herein, the adjuster section alters the intensity of a portion of the radiation emitting radially from the radiation source when a portion of the radiation source is positioned in the vessel. In use, the adjuster section partly alters the intensity of radiation directed at where the vessel lamina is the closest. This prevents overtreatment of the vessel.

As used herein, the term "radiation dose profile" refers to and means a cross-sectional pattern of energy being delivered to the vessel from a radiation source. A more comprehensive definition of radiation dose profile is provided in the description section.

As used herein, the term "vessel wall" refers to and means the structural support of the vessel. For an artery, the vessel wall includes an endothelium, a basement membrane, a vessel intima, an internal elastic lamina, a vessel media, a vessel external elastic lamina (hereinafter "vessel lamina"), and a vessel adventitia. For a diseased artery, the vessel wall can also include atherosclerotic plaque which infiltrates the vessel intima and causes stenosis of the vessel.

The adjuster section alters a portion of the radiation emitting radially from the radioactive source so that a radiation dose profile which is substantially asymmetrical and eccentric is delivered to the vessel. With an eccentric, asymmetrical radiation dose profile, more radiation is directed at where the vessel lamina is farthest from the radiation source, while less radiation is delivered to where the vessel lamina is the closest. Thus, a substantially uniform dosage of radiation can be delivered to the vessel lamina at the treatment site, even though the delivery device is not centered in the vessel relative to the vessel lamina.

In one version of the present invention, the adjuster section includes a plurality of spaced apart conductor coils which create a magnetic field proximate to the radiation source. Depending upon the direction of current through each conductor coil, each coil either attenuates or potentiates the charged particle radiation which emits from the radiation source. Further, the amount of attenuating or potentiating for each conductor coil depends upon the magnitude of the current in each conductor coil. Thus, the radiation dose profile relative to the radiation source can be specifically tailored for a particular vessel by adjusting the magnitude and direction of current in each conductor coil.

Typically, conductor coils are attached to a catheter and spaced apart radially around the catheter. Additionally, the conductor coils can be spaced apart longitudinally along the catheter. This feature allows the radiation dose profile along a longitudinal axis of the radiation source to be modified so that the radiation dose profile along the radiation source is varied. Thus, the radiation dose delivered to the vessel can be accurately tailored to suit the shape of a treatment site.

In another version, the adjuster section can be an attenuator section which includes an attenuator material. The attenuator material at least partly diminishes the intensity of the radiation which emits radially from the radiation source. The attenuator material is typically a relatively dense material having a relatively high atomic number. Preferably, the attenuator material is also bio-compatible and safe for use in surgery. Materials such as gold, platinum, and tantalum can be used. Additionally, the attenuator section can be divided into a plurality of spaced apart, attenuator segments, so that the adjuster section is more flexible and easier to move through a curved vessel.

Importantly, the design of the adjuster section determines the shape of the radiation dose profile which is delivered to the vessel. Thus, the present invention can be utilized to provide an accurate dose of radiation to a treatment site.

As used herein, the phrase "configuration of the attenuator section" shall mean the size, shape, thickness, and material utilized in the attenuator section. Also as used herein the phrase "configuration of the vessel wall" shall mean the size and shape of the vessel wall at the treatment site, including the positioning of the vessel lamina relative to the vessel lumen, and the shape and size of the atherosclerotic plaque.

Preferably, the device also includes an imager which is secured proximate to the adjuster section. The imager allows for substantially real time images of the vessel prior to and during treatment with radiation. This embodiment is preferred so that the position of the adjuster section in the vessel can be constantly monitored during treatment with radiation. This allows the doctor performing the procedure to correct deficiencies which may arise in the positioning of the adjuster section.

The invention is also a method for delivering radiation from a radiation source to a treatment site of a vessel. The method includes the steps of positioning the radiation source in the vessel and creating a magnetic field within the vessel, so that the radiation source delivers a radiation dose profile in the vessel relative to the radiation source which is substantially asymmetrical.

Further, the invention can also include the step of altering the radiation emitting from the radiation source, so that the radiation dose profile also varies along the longitudinal axis of the radiation source. This feature allows the dose of radiation delivered to the treatment site to be accurately tailored longitudinally to suit the needs of the patient.

In alternate embodiments, some of the features outlined above can be directly incorporated into the radiation source and/or the radiation source can be a stent. Further, a controller can be utilized which receives the images from the imager and provides a treatment plan for the treatment site.

It is important to recognize that with the present invention, the vessel receives a radiation dose profile which is substantially asymmetrical relative to the radiation source. Therefore, the radiation source is able to deliver a substantially uniform dose to the vessel lamina, even though the radiation source is not centered relative to the vessel lamina. Further, the radiation delivered to the vessel can be specifically tailored to suit the configuration of the vessel wall at the treatment site.

BRIEF DESCRIPTION OF THE DRAWINGS

The novel features of this invention, as well as the invention itself, both as to its structure and its operation will be best understood from the accompanying drawings, taken in conjunction with the accompanying description, in which.

DESCRIPTION

Figure 1:
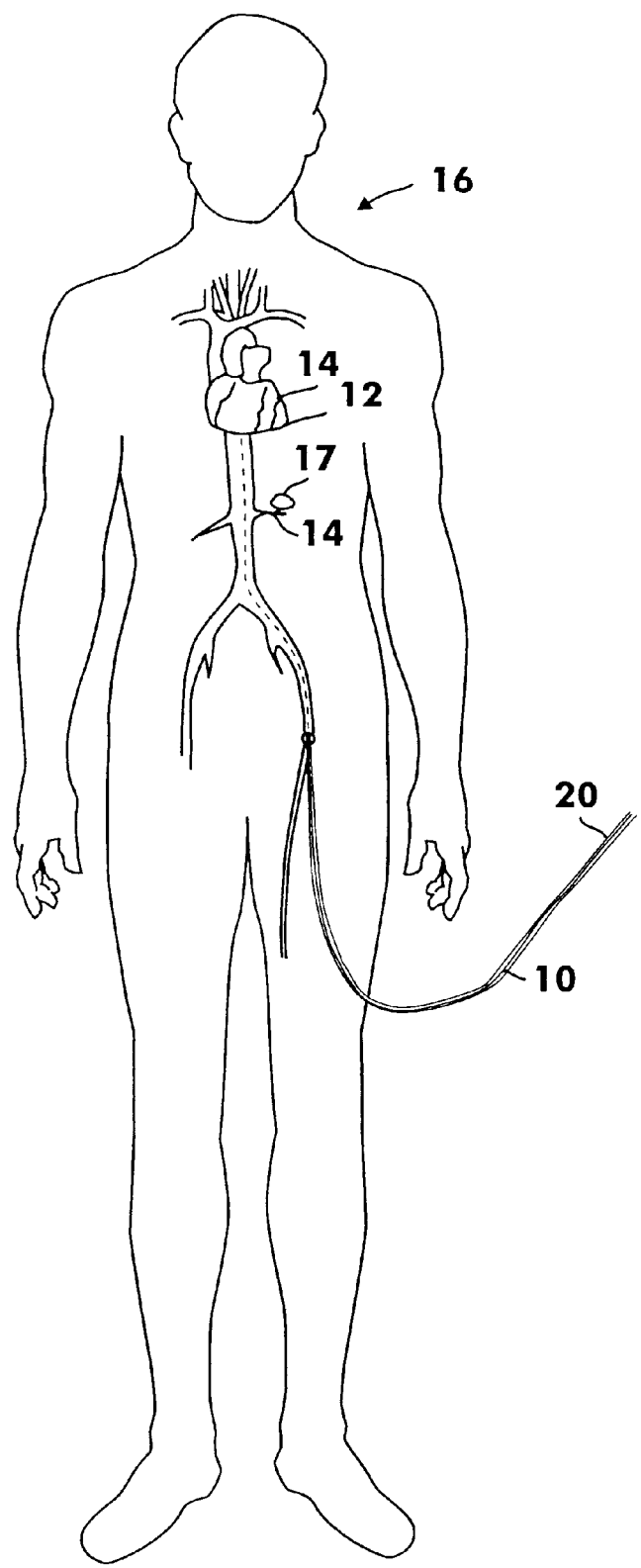
FIG. 1 is a top plan view of a patient with a device having features of the present invention positioned in a vessel of the patient.

Referring initially to FIG. 1, a device 10 for providing a dosage of radiation to a treatment site 12 of a vessel 14 of a patient 16 is provided herein. The device 10 is useful for treating a tubular treatment site 12 of a vessel wall 18 (shown in FIGS. 3 and 4) of a vessel 14 throughout the vascular system of the patient 16. Although the present invention is particularly useful for inhibiting the re-growth of neointima in coronary arteries, it is anticipated that the present device 10 can be used to treat other medical conditions, such as cancer 17, proximate the vessel 14.

The device 10 may be introduced into the vessel 14 wherever it is convenient. As shown in FIG. 1, the device 10 can be inserted through an external, flexible tubular shield 20 which partly inhibits the intensity of radiation. The tubular shield 20 diminishes the potential of radiation exposure to the medical staff during use of the present device 10. A guiding catheter (not shown) is typically used in conjunction with the present device 10 for the treatment of coronary arteries. A suitable guiding catheter is sold by various vendors, including Medtronic® of Minneapolis, Minn.

Figure 2:
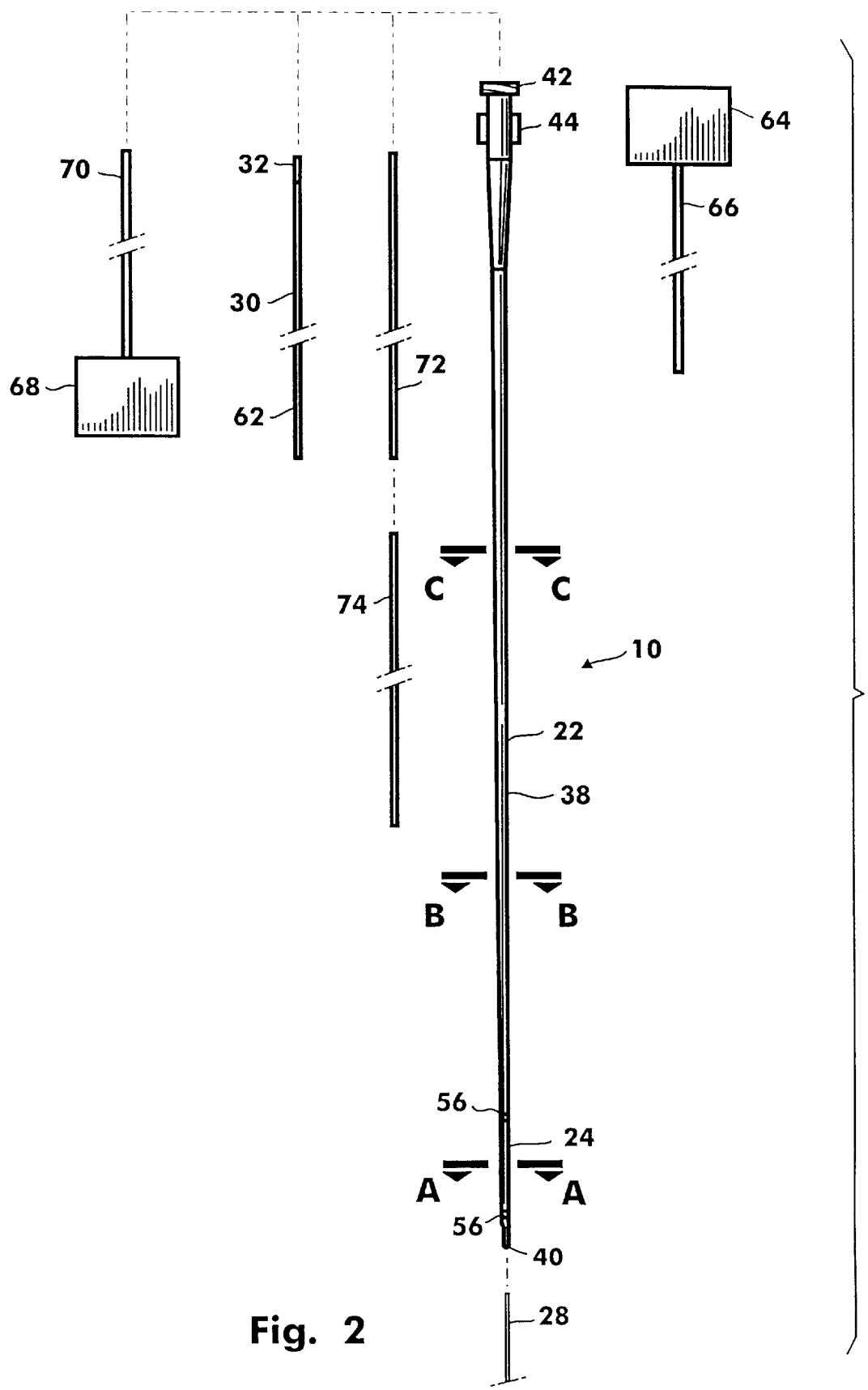
FIG. 2 is an exploded, side plan view of a device having features of the present invention.

The structural details of a first embodiment of the device 10 may be seen in FIG. 2, where the device 10 includes a catheter 22, a delivery section 24, a catheter supporter 26 (not shown in FIG. 2), a guidewire 28 and a radiation source 30 having a radioactive segment 32.

As provided in detail below, the present invention allows the doctor to specifically control the intensity of the radiation which is delivered to various portions of the vessel wall 18. For example, the present invention can be used to deliver a less intense dose of radiation where the vessel wall 18 is closest to the radiation source 30. This allows the doctor to tailor the radiation treatment to suit the configuration of the vessel wall 18 at the treatment site 12. Further, this allows the doctor to deliver a precise, substantially uniform dose of radiation to a vessel lamina 34 to inhibit the growth of neointima in the vessel 14.

It is anticipated that the present invention will be used in conjunction with other vascular procedures such as angioplasty, stenting, and/or atherectomy for the treatment of a stenosis 33 in the vessel 14. However, the present device 10 can also be used in lieu of these or other procedures.

Figure 3:
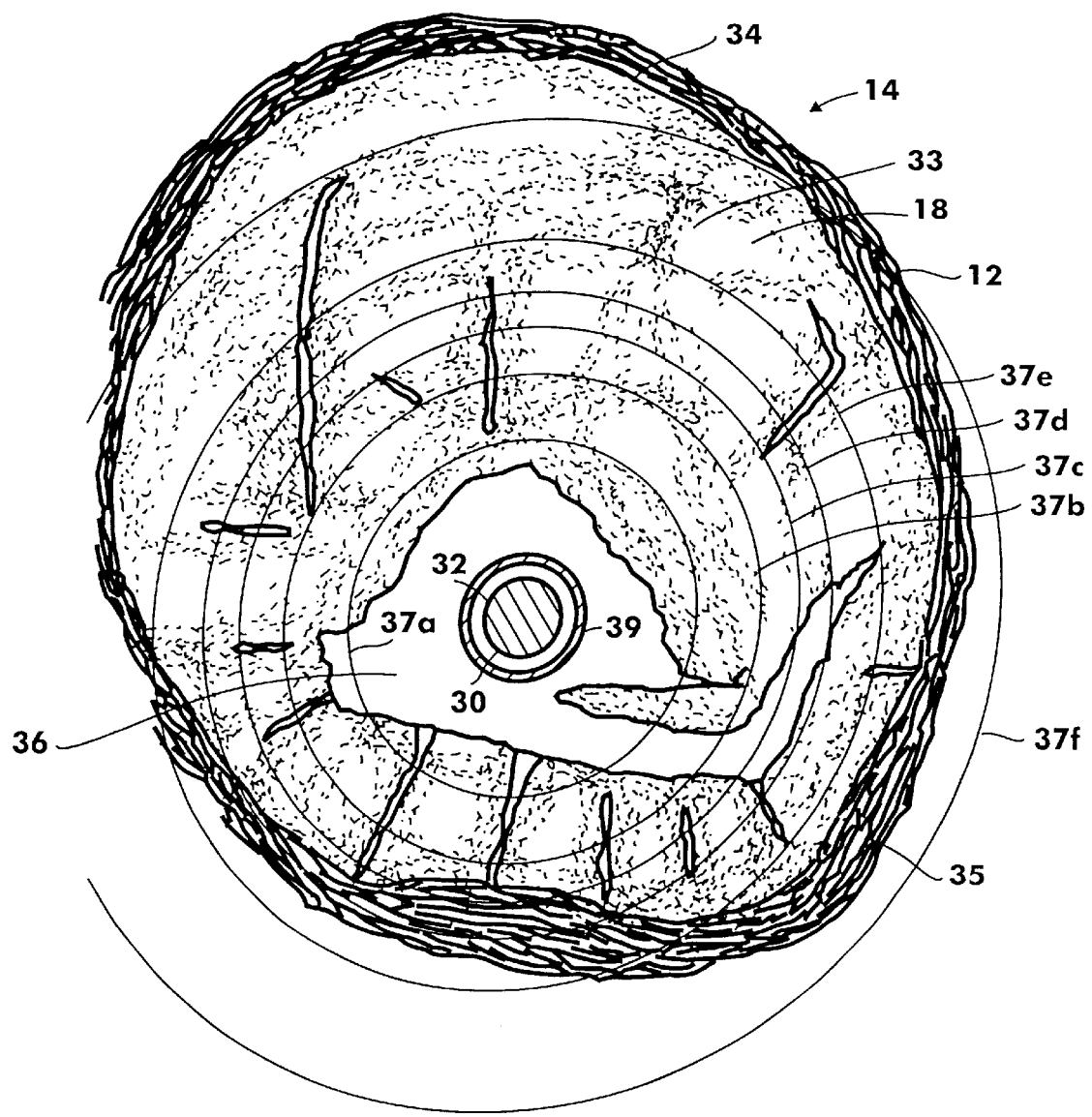
FIG. 3 is a cross-sectional view of a prior art delivery device positioned in a vessel.
Figure 4:
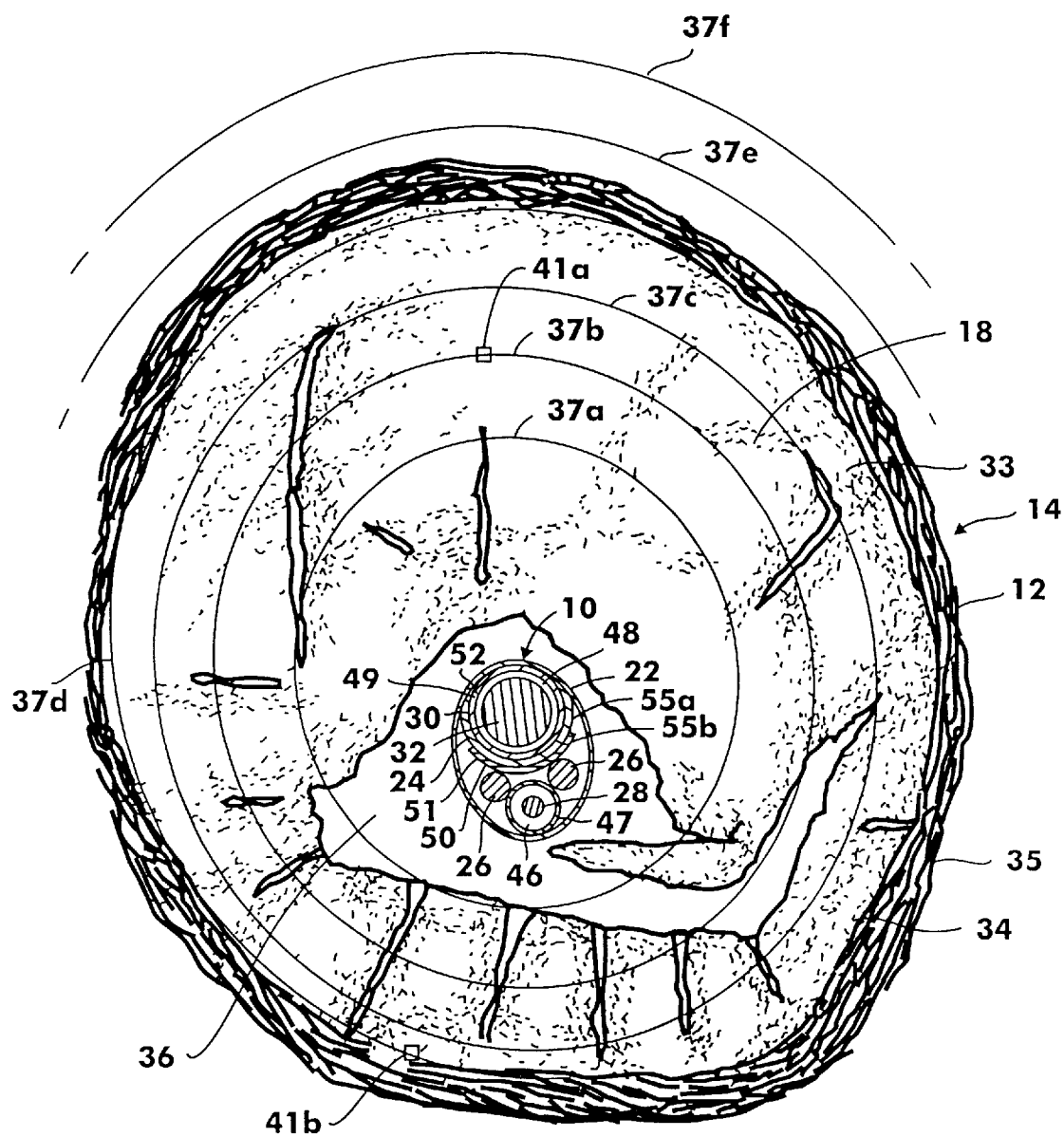
FIG. 4 is a cross-sectional view of a device having features of the present invention positioned in a vessel.

Referring to FIGS. 3 and 4, the vessel wall 18 includes the stenosis 33, a vessel lamina 34, and a vessel adventitia 35. The configuration of the vessel wall 18 defines the size and shape of a vessel lumen 36 and the location of the vessel lumen 36 relative to the vessel lamina 34. In the vessel 14 shown in FIGS. 3 and 4, the vessel wall 18 is irregular, asymmetrical, and oblong shaped. Thus, the vessel lumen 36 is offset from center and eccentrically positioned relative to the vessel lamina 34. Therefore, the device 10 positioned in the vessel lumen 36, is offset from center and eccentrically positioned relative to the vessel lamina 34. It should be noted that the vessel lumen 36 represented in FIGS. 3 and 4 is the resulting vessel lumen 36 after an angioplasty treatment.

There is considerable debate about the amount of radiation that should be delivered to the vessel 14 to inhibit the growth of neointima. The present invention is designed to deliver a dosage of approximately ten (10) to twenty (20) gray of radiation to the vessel lamina 34. However, the present invention is not intended to be limited to these dosages and the dosages provided herein are only exemplary. For example, additional research may determine that dosages of more than or less than ten (10) to twenty (20) gray may be more beneficial to the patient 16.

As used herein, the term radiation dose profile refers to and means the cross-sectional pattern of energy being delivered by the radiation source 30 to the vessel 14. The approximate shape of the radiation dose profile is represented by a plurality of isodose curves 37A–F shown in FIGS. 3 and 4 which encircle the radiation source 30. Each isodose curve 37A–F represents an approximate area in the vessel 14 which is receiving a substantially uniform dosage of radiation during treatment. For example, isodose curve 37A can represent the area in the vessel 14 which receives a dosage of approximately thirty (30) gray, isodose curve 37B can represent the area in the vessel 14 which receives a dosage of approximately twenty-five (25) gray, isodose curve 37C can represent the area of the vessel 14 which receives a dosage of approximately twenty (20) gray, isodose curve 37D can represent the area of the vessel 14 which receives a dosage of approximately fifteen (15) gray, isodose curve 37E can represent the area in the vessel 14 which receives a dosage of approximately ten (10) gray, and isodose curve 37F can represent the area in the vessel 14 which receives a dosage of approximately five (5) gray.

FIG. 3 shows the isodose curves 37A–F from a prior art delivery device 39. For the prior art delivery device 39, the radiation emits substantially equally radially from the radiation source 30. Thus, the isodose curves 37A–F in FIG. 3, are substantially circular and concentric relative to the radiation source 30. FIG. 3 illustrates that the vessel lamina 34 does not receive a substantially uniform dosage with the prior art delivery device 39. In fact, portions of the vessel lamina 34 receive a dosage of approximately twenty (20) gray, while other portions of the vessel lamina 34 receive a dosage of less than five (5) gray. Thus, depending upon the actual dosage utilized, portions of the vessel lamina 34 may be under-treated, while other portions of the vessel lamina 34 will be over-treated.

FIG. 4 illustrates one example of the isodose curves 37A–F which can be obtained utilizing a device 10 having features of the present invention. Because of the unique design provided herein, the isodose curves 37A–F in FIG. 4 are not circular. In fact, the isodose curves 37A–F in FIG. 4 are substantially elliptical, eccentric, and asymmetrical relative to the radiation source 30. As a result thereof, referring to isodose curve 37D of FIG. 4, the entire vessel lamina 34 receives a substantially uniform dose of approximately fifteen (15) gray, even though the delivery device 10 is not centered relative to the vessel lamina 34.

As illustrated in FIG. 4, the device 10 can be designed so that at least two (2) equidistant, substantially diametrically opposed points, within the vessel 14, relative to the radiation source 30 on the radiation dose profile receive a different dosage of radiation. The difference in the amount of radiation dosage depends upon the design of the device 10. It is believed that a device 10 can be designed so that the two (2) equidistant, diametrically opposed points within the vessel 14 on the radiation dose profile differ between approximately at least one percent to ninety-nine percent (1%–99%), preferably between approximately ten percent to sixty percent (10%–60%) and more preferably between approximately twenty percent to forty percent (20%–40%). A representative pair of substantially diametrically opposed points 41a and 41b, substantially equally distanced from the radiation source 30 are illustrated as blocks for clarity in FIG. 4. One point 41a is positioned on isodose curve 37B while the other point 41b is positioned on isodose curve 37C. Thus, for the example provided herein, point 41a receives a dosage of approximately twenty-five (25) gray while the other point 41b receives approximately twenty (20) gray.

In some embodiments, the catheter 22 is used to position the radioactive source 30 adjacent to the treatment site 12. The catheter 22 includes a tubular outer structure 38 having a catheter distal end 40 and a catheter proximal end 42. The catheter distal end 40 inserts into the vessel lumen 36 and should be as smooth as possible to facilitate insertion into the vessel lumen 36. The catheter proximal end 42 typically remains outside the patient 16. As shown in FIG. 2, the catheter proximal end 42 can include a handle 44 which is used to manipulate and rotate the catheter 22 in the vessel lumen 36.

The outer structure 38 can be made from a variety of materials, such as a block copolymer sold under the trademark Pebax® by Elf Atochem North American located in Philadelphia, Pa. or polyethylene. Preferably, the outer structure 38 is coated with a hydrophilic or other lubricious coating to facilitate easy movement of the catheter 22 in the vessel lumen 36.

As illustrated in FIGS. 4–7, the catheter 22 can include a guidewire lumen 46 for receiving the guidewire 28. The guidewire lumen 46, shown in these Figures, is defined by a guidewire tube 47 having an inner diameter of between about 0.015 inches to 0.025 inches. The guidewire lumen 46 extends from the catheter proximal end 42 to the catheter distal end 40.

The catheter 22 illustrated in FIGS. 4–7 also includes a delivery lumen 48 which is sized and shaped to receive the radiation source 30. Thus, the size and shape of the delivery lumen 48 depends upon the size and shape of the radiation source 30. In the embodiment shown in the Figures, the delivery lumen 48 is defined by a delivery tube 49 having an inner diameter of between about 0.02 inches to 0.03 inches. The delivery lumen 48 extends from the catheter proximal end 42 to proximate the catheter distal end 40. The delivery lumen 48 can be sealed proximate the catheter distal end 40 to prevent the radiation source 30 from escaping into the vessel 14 and to prevent direct contact between the blood (not shown) in the vessel 14 and the radiation source 30. Alternately, the delivery lumen 48 can be open proximate the catheter distal end 40. The delivery tube 49 and the guidewire tube 47 can be made from a number of materials, including a block copolymer or a high density polyethylene.

It is anticipated that the catheter 22 can also include a bypass lumen (not shown) for transporting blood (not shown) in the vessel 14, past the catheter 22, when the catheter 22 is positioned in the vessel 14. Basically, the bypass lumen allows the delivery device 10 to be used in relatively small vessels 14 without interrupting blood flow in the vessel 14.

In the embodiment shown in FIGS. 4–7, the delivery section 24 receives the radioactive segment 32. In this embodiment, the delivery section 24 causes the vessel 14 to receive a radiation dose profile which is substantially asymmetrical, eccentric, and elliptical relative to the radiation source 30. Thus, a substantially homogenous radiation dose can be delivered to the vessel lamina 34 at the treatment site 12 even though the delivery device 10 is eccentrically positioned relative to the vessel lamina 34.

The length and positioning of the delivery section 24 can be varied to meet the needs of the patient 16. Typically, the delivery section 24 is approximately one half centimeter to ten centimeters (0.5 cm.–10 cm.) centimeters long and is positioned proximate the catheter distal end 40. The delivery section 24 can include an adjuster section 51 for altering the intensity of the radiation emitting from the radiation source 30. In the embodiment shown in FIGS. 4–7, the adjuster section 51 includes an attenuator section 50 for altering the intensity of radiation emitting radially from the radiation source 30 and a window section 52. Basically, the attenuator section 50 alters the pattern of radiation emitting radially from the radiation source 30 to compensate for the irregular shape of the stenosis 33 and for the eccentric positioning of the radiation source 30 relative to the vessel lamina 34.

The attenuator section 50 can be designed to attenuate approximately between about one percent to one hundred percent (1%–100%) of the intensity of the radiation directed toward the attenuator section 50. In contrast, the window section 52 can be designed to attenuate approximately between zero percent to ninety-nine percent (0%–99%) of the intensity of the radiation directed at the window section 52.

Typically, the attenuator section 50 attenuates a relatively significant amount of radiation directed towards the attenuator section 50 while the window section 52 has a relatively negligible or insignificant effect upon the radiation emitting from the radiation source 30. For example, the attenuator section 50 can attenuate approximately between ten percent to forty percent (10%–40%) of the intensity of radiation directed at the attenuator section 50 while the window section 52 attenuates less than approximately one percent (1%) of the intensity of the radiation directed at the window section 52.

Importantly, in this embodiment, it is the difference in the amount of attenuating between the window section 52 and the attenuator section 50 that is significant in determining the radiation dose profile. Conceivably, the attenuator section 50 can attenuate between about one percent to one hundred percent (1%–100%) more radiation than the window section 52 to create isodose curves 37A–F which are asymmetrical and not circular relative to the radiation source 30. Typically, for most situations, the attenuator section 50 is designed to attenuate about five percent to ninety percent (5%–90%) and more preferably about ten percent to forty percent (10%–40%) more radiation than the window section 52.

Alternately, to deliver a concentrated dosage of radiation to a specific area, i.e., cancer 17 proximate the vessel 14, the attenuator section 50 can be designed to attenuate between about ninety percent to one hundred percent (90%–100%) more radiation than the window section 52.

In the embodiment shown in FIGS. 4–7, the attenuator section 50 includes a portion of the delivery tube 49, a first component 55a, and a second component 55b. The first and second components 55a, 55b include an attenuator material which attenuates the intensity of radiation therethrough. In contrast, the delivery tube 49 is made of a material which has a relatively insignificant or immeasurable effect upon the radiation.

Importantly, the configuration of the attenuator section 50, i.e., the size, shape, thickness, and the attenuator material of the attenuator section 50 can be varied to change the shape of the radiation dose profile to suit the configuration of the vessel wall 18 at the treatment site 12. For example, as the size and thickness of the attenuator section 50 increases, the radiation dose profile becomes increasingly more eccentric and more asymmetrical. Similarly, as the size and thickness of the attenuator section 50 is decreased, the radiation dose profile becomes increasingly more concentric.

Figures 5, 6A, 6B:
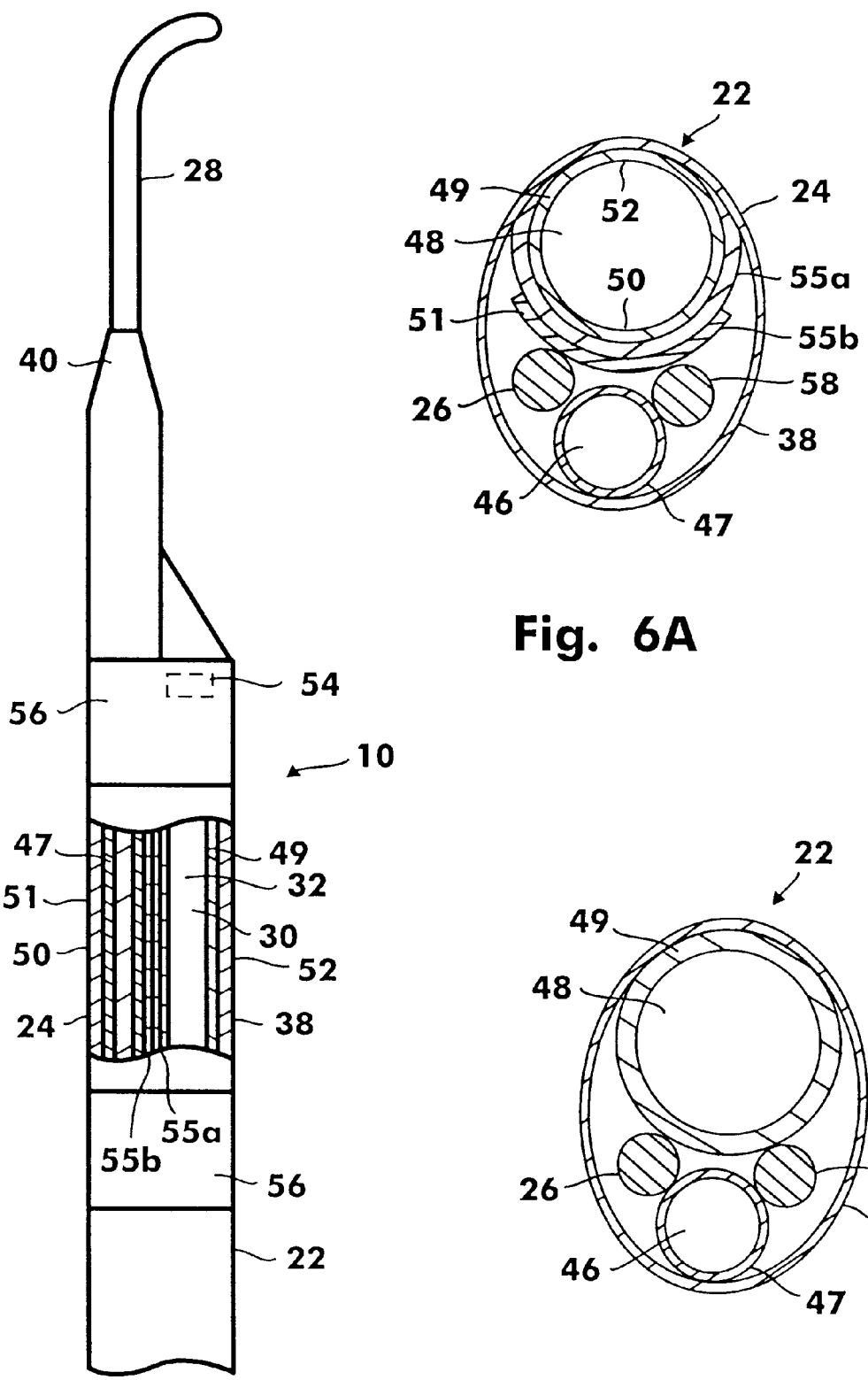
FIG. 5 is an enlarged view, in partial cutaway, of a portion of a delivery device having features of the present invention.
FIG. 6A is a cross-sectional view of a first embodiment of a catheter taken on Line A—A in FIG. 2.
FIG. 6B is a cross-sectional view of the first embodiment of the catheter taken on Line B—B in FIG. 2.
Figure 8:
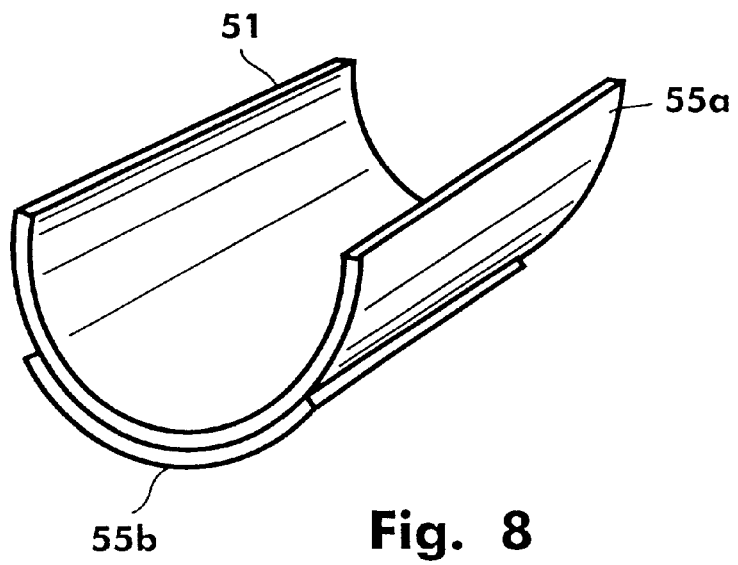
FIG. 8 is an enlarged, perspective view of a portion of an attenuator section having features of the present invention.
Figure 10:
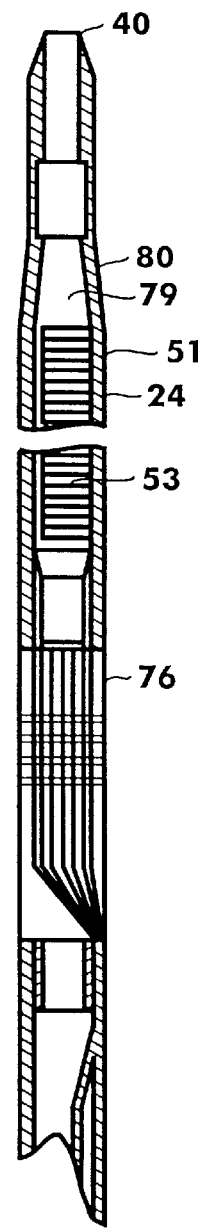
FIG. 10 is an enlarged cut-away view of a portion of the catheter of FIG. 9.

As illustrated in FIGS. 5 and 8, the attenuator section 50 can be a continuous piece of attenuator material. Alternately, as shown in FIG. 10, the attenuator section 50 can be a plurality of adjacent, discrete attenuator segments 53 which allow the delivery section 24 to be more flexible and easier to move in tortuous vessels 14. In this embodiment, each attenuator segment 53 is semicircular and between approximately one-quarter millimeter to one millimeter (0.25 mm.–1.0 mm.) wide.

The attenuator material can be made from a number of materials and/or alloys which attenuate radiation. Because of the size limitations of the device 10, the attenuator material is typically a relatively dense material having a relatively high atomic number. Preferably, to minimize the size of the attenuator section 50, the attenuator material has: (i) a density of at least about ten (10) grams per cubic centimeter and more preferably at least about nineteen (19) grams per cubic centimeter; and (ii) an atomic number of at least about twelve (12), and more preferably at least about seventy (70). Further, the attenuator material is preferably bio-compatible so that the attenuator section 50 is compatible with the vessel 14. It is anticipated that gold, platinum, or tantalum can be used as the attenuator material. Alternately, alloys utilizing one or more relatively dense materials can also be used.

Referring to FIG. 8, the first and second components 55a, 55b are each a piece of thin foil that is between about one (1) to one thousand (1,000) microns and more preferably between about five (5) to fifty (50) microns thick. Each of the first and second components 55a, 55b are shaped similar to a semi-circular band. In this embodiment, the first component 55a is rolled or wrapped around a portion of the delivery tube 49 while the second component 55b is rolled or wrapped around the first component 55a. The first component 55a can be bonded to the delivery tube 49 and the second component 55a can be bonded to the first component 55a with a suitable adhesive. Alternately, a retaining tubular conduit (not shown) can be wrapped around and retain the first and second components 55a, 55b to the delivery tube 49.

As shown in FIGS. 4, 6A, 7, and 8 the first component 55a can extend approximately two hundred degrees (200°) around the delivery tube 49 while the second component 55b can extend approximately one hundred and twenty degrees (120°) around the delivery tube 49. It is anticipated that the first component 55a can be designed to extend between about two hundred degrees to two hundred and seventy degrees (200°–270°), while the second component 55b extends between about one hundred degrees to one hundred and fifty degrees (100°–150°). Further, the positioning of the first and second components 55a, 55b can be switched. Alternately, the attenuator section 50 can be implemented in a number of other ways. For example, the attenuator section 50 can be a thin foil of varying thickness, which is rolled completely around or partly around the delivery tube 49. In this embodiment, the foil can include an opening (not shown) which forms the window section 52. Alternately, the attenuator material can be sputtered and then electroplated directly onto the delivery tube 49 or ion beam technology can be used to secure the attenuator material to the delivery tube 49. Further, it is envisioned that the delivery tube 49 could be impregnated with an attenuator material such as barium.

It is also anticipated that a plurality of different devices 10 can be provided to the hospital and each device 10 will have an attenuator section 50 with a different attenuator configuration. Thus, the doctor will be able to choose the device 10 having the radiation dose profile which most closely matches the configuration of the vessel wall 18.

Figure 7:
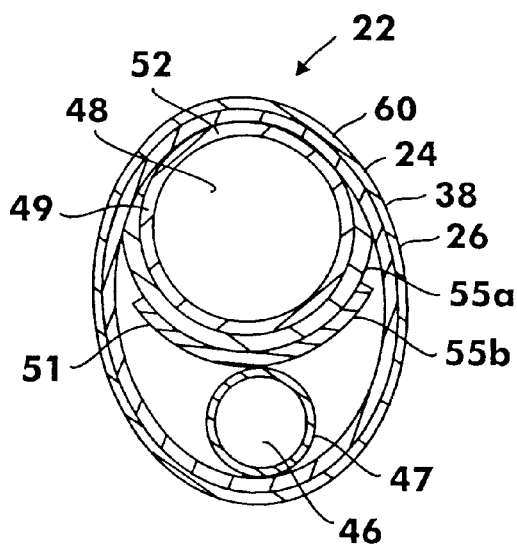
FIG. 7 is a cross-sectional view of a second embodiment of a catheter.

As can best be seen with reference to FIGS. 6A and 7, the window section 52 illustrated in the Figures is defined by the portion of the delivery tube 49 which is not covered with the attenuator material. Typically, the delivery tube 49 is made of a material which has a negligible, insignificant, and biologically immeasurable effect upon the radiation emitting from the delivery section 24 when compared to the attenuator section 50. In fact, because the attenuator section 50 also includes a portion of the delivery tube 49, the window section 52, in this embodiment, basically has no relative effect upon the radiation emitting from the delivery section 24.

Because the window section 52 does not reduce the intensity of the radiation as much as the attenuator section 50, the radiation emitting from the window section 52 reaches a greater depth in the tissue than radiation emitting from the attenuator section 50. This enables the device 10 to preferentially deliver more radiation to where the vessel lamina 34 is the furthest.

Referring back to FIG. 4, in use, the delivery section 24 is rotated in the vessel lumen 36 until the attenuator section 50 is substantially closest to the vessel lamina 34, while the window section 52 is farthest from the vessel lamina 34. In most instances, the attenuator section 50 is proximate where the vessel wall 18 is the thinnest while the window section 52 is proximate where the vessel wall 18 is the thickest.

The catheter 22 can include a radiation blocker 54 (shown in phantom in FIG. 5) positioned proximate the catheter distal end 40 which inhibits radiation from emitting longitudinally from the delivery section 24. The radiation blocker 54, for example, can be a cylindrical disk made from a relatively dense material such a platinum or gold which is positioned in the delivery conduit proximate the catheter distal end 40.

Preferably, the device 10 includes a pair of markers 56 which assist in the positioning of the delivery section 24 proximate the treatment site 12. Referring to the Figures, the markers 56 can each be a band, made from a radiopaque material, which encircles the outer structure 38 of the catheter 22 on each side of the delivery section 24. Because the markers 56 are made of a radiopaque material, such as platinum or gold, the position of the markers 56 is visible using a fluoroscope or x-rays.

The catheter supporter 26 inhibits rotational deformation or twisting of the catheter 22 between the catheter distal end 40 and the catheter proximal end 42. In use, the catheter supporter 26 transmits torque smoothly and predictably between the catheter proximal end 42 and the catheter distal end 40. This allows the delivery section 24 to be precisely rotated with the handle 44 so that the window section 52 is farthest away from the vessel lamina 34 at the treatment site 12.

Figure 6C:
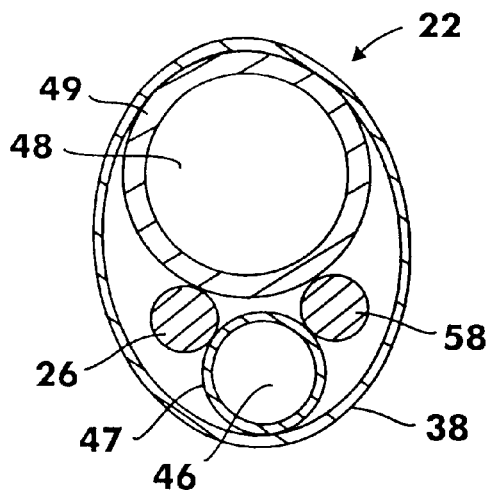
FIG. 6C is a cross-sectional view of the first embodiment of the catheter taken on Line C—C in FIG. 2.

The catheter supporter 26 can be implemented in a number of alternate ways. For example, as shown in FIGS. 6A–C, the catheter supporter 26 can include a pair of spaced apart cylindrical shafts 58 positioned within the catheter outer structure 38 and extending substantially parallel with the guidewire lumen 46 and the delivery lumen 48. The cylindrical shafts 58 are widest proximate the catheter proximal end 42 and taper towards the delivery section 24.

Alternately, as shown in FIG. 7, the catheter supporter 26 can be a tubular member 60 which encompasses the guidewire lumen 46 and the delivery lumen 48. The tubular member 60 is positioned within the catheter outer structure 38 and is substantially concentric with the catheter outer structure 38. Similarly, the tubular member 60 is thickest proximate the catheter proximal end 42 and tapers towards the delivery section 24. With the disclosure provided herein, those skilled in the art will recognize other ways to design the catheter supporter 26.

The catheter supporter 26 must be sufficiently flexible to allow the catheter 22 to be positioned in small, curving vessels 14. The catheter supporter 26 can be made of a number of materials which include a composite of polymer and metallic components. For example, a suitable catheter supporter 26 can be made from the block copolymer sold under the trademark Pebax® by Elf Atochem. The catheter supporter 26 provided herein also inhibits the guidewire lumen 46 and the delivery lumen 48 from collapsing.

The guidewire 28 inserts into the vessel lumen 36 and guides the delivery section 24 through the vessel lumen 36 to the treatment site 12. A guidewire 28 having a diameter of about 0.014 inches is commonly used.

The radiation source 30 illustrated in FIGS. 2 and 5 is sized to fit into the delivery lumen 48 and includes a delivery wire 62 and the radioactive segment 32 attached to the delivery wire 62. The radiation source 30 inserts into the delivery section 24 and remains in the delivery section 24 until the proposed dosage is released. Thus, the amount of time that the radiation source 30 is positioned in the delivery section 24 depends upon the emittance of the radioactive segment 32, the adjuster section 51 utilized, and the proposed dosage requirements of the patient 16.

Preferably, the radioactive segment 32 emits β-rays because the β-rays have a relatively short tissue penetration. With the short tissue penetration of β-rays, the medical staff is exposed to less radiation and the β-rays can be controlled within the delivery section 24. Preferably, the radioactive segment 32 also has a relatively high activity level so that the prescribed dose of radiation emits quickly into the patient 16. For example, a radioactive segment 32 which includes Rhenium could have an activity level of about 2 to 300 mCi and a usable tissue penetration of up to approximately four and one-half millimeters (4.5 mm). Typically, the radioactive segment 32 is between about one-half centimeter (0.5 cm) to ten centimeters (10.0 cm) in length and has a diameter of between approximately one-tenth millimeter (0.1 mm) to two millimeters (2.0 mm). Additionally, the radioactive segment 32 can be rechargeable and reusable to minimize radioactive waste.

Alternately, it is anticipated that the radioactive segment 32 could include gamma emitters or a non-nuclear source could provide the radioactivity to the radioactive area 32.

Typically, the device 10 illustrated in FIG. 2 is used in conjunction with a first imaging system 64 which provides an accurate and detailed map or image of the internal structure of the vessel 14. A suitable first imaging system 64 is an Intravascular Ultrasound System ("IVUS System") which uses ultrasonic waves to map or image the vessel 14. The first imaging system 64 includes a first imaging catheter 66 which inserts directly into the vessel lumen 36 to image the structure of the vessel 14.

Further, the device 10 illustrated in FIG. 2 can be used in conjunction with a second imaging system 68 which indicates when the delivery section 24 is properly oriented within the vessel lumen 36. An IVUS System can also be used for the second imaging system 68. Referring to FIG. 2, the second imaging system 68 includes a second imaging catheter 70 which inserts into the delivery lumen 48 to determine when the delivery section 24 is properly oriented. If the second imaging system 68 is an IVUS System, the delivery lumen 48 must be filled with a substantially incompressible fluid (not shown), such as saline. It is anticipated that the same IVUS System can be used for the first imaging system 64 and the second imaging system 68.

In the embodiment shown in FIG. 2, a sheath 72 can be used to protect or isolate the radiation source 30 from the incompressible fluid. The sheath 72 can be a tubular cover which inserts into the delivery lumen 48. The sheath 72 provides a barrier and isolates the radiation source 30 from contact with the incompressible fluid. The sheath 72 can be made of a thin, high density polyethylene.

The device 10 illustrated in FIG. 2 can also include a dummy rod 74 for inserting the sheath 72 into the delivery lumen 48 and insuring that the delivery lumen 48 is not collapsed. The dummy rod 74 is designed to be substantially identical to the radiation source 30. Basically, the dummy rod 74 is used to install the sheath 72 and insure that the radiation source 30 will move smoothly within the delivery lumen 48 to the delivery section 24.

Figure 9:
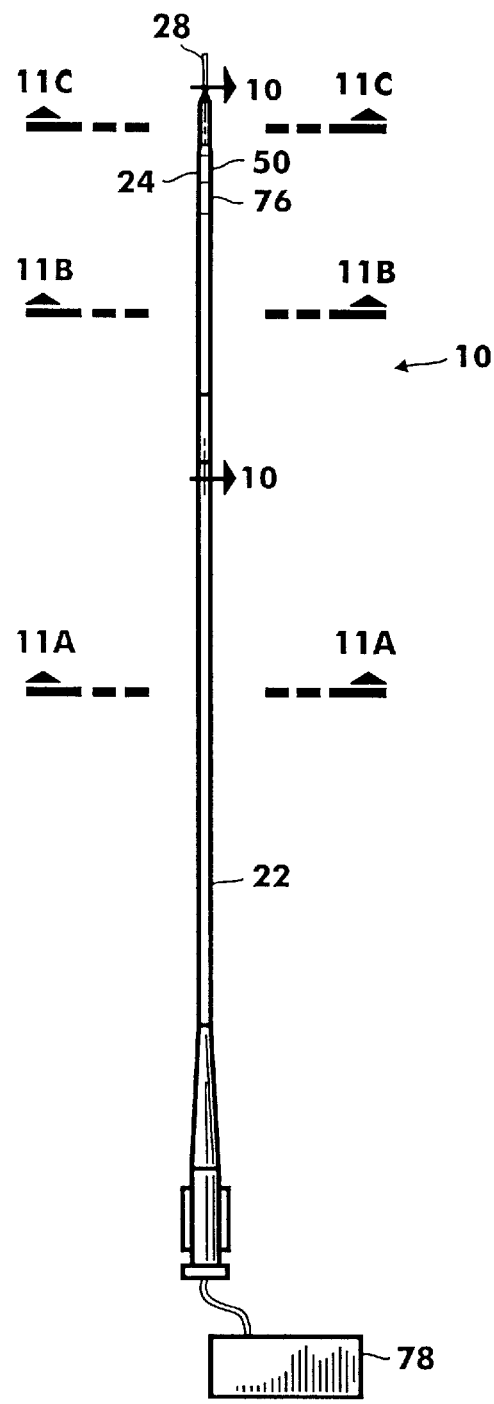
FIG. 9 is a side plan view of another embodiment of a catheter having features of the present invention.

Referring now to FIGS. 9–11, an alternate embodiment of the present invention utilizes an open-ended catheter 22 having the attenuator section 50, an imager 76, and a controller 78. In this embodiment, the catheter 22 utilizes a single lumen 79 which initially receives the guidewire 28 for positioning the catheter 22 in the vessel 14. Subsequently, the guidewire 28 is removed and the radiation source 30 is inserted into the single lumen 79. The catheter distal end 40, in this embodiment, is open and includes a tapered section 80, distal to the attenuator section 50 for inhibiting the movement of the radiation source 30 out the open end of the catheter 22. The tapered section 80 has an inner diameter which is larger than the diameter of the guidewire 28 but less than the diameter of the radiation source 30. This allows the guidewire 28, but not the radiation source 30, to pass through the tapered section 80.

Figure 11A:
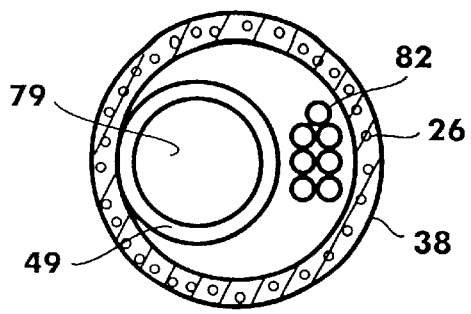
FIG. 11A is a cross-sectional view taken on Line 11A—11A in FIG. 9.
Figure 11B:
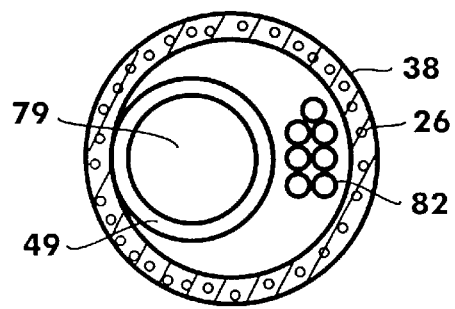
FIG. 11B is a cross-sectional view taken on Line 11B—11B in FIG. 9.
Figure 11C:
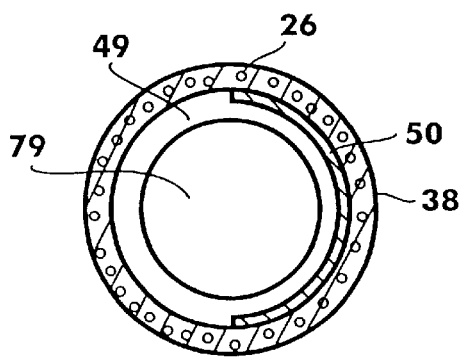
FIG. 11C is a cross-sectional view taken on Line 11C—11C in FIG. 9.
Figure 12:
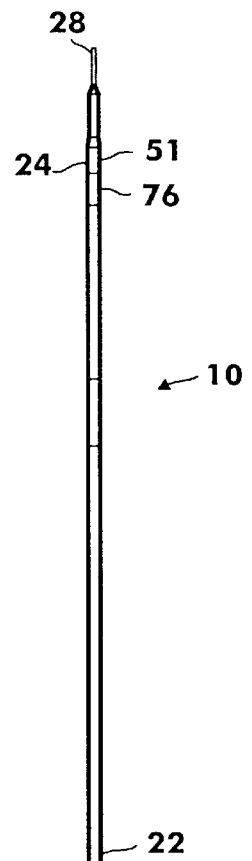
FIG. 12 is a side plan view of yet another embodiment of a catheter having features of the present invention.
Figure 12:

In the embodiment illustrated in FIGS. 9–11, the attenuator section 50 includes the plurality of adjacent semi-circular attenuator segments 53. These attenuator segments 53 allow the delivery section 24 to be more flexible for movement in a tortuous vessel 14. As illustrated in FIGS. 11A–11C, the catheter supporter 26 is integrated into the catheter outer structure 38. Thus, the catheter outer structure 38 can, for example, include a plurality of stainless steel bands which facilitate the rotation of the catheter distal end 40 to properly orientate the catheter 22.

The imager 76, in this embodiment, is built into and secured to the catheter 22. The imager 76 provides a substantially real time image of the cross section of the vessel 14. Because the imager 76 is secured to the catheter 22, the imager 76 can be used to continuously monitor the position of the catheter 22 and/or the adjuster section 51 during the procedure in the vessel 14. Therefore, the imager 76 can be used to insure that there is no movement of the catheter 22 during the procedure and that the attenuator section 50 is properly oriented so that the appropriate dosage is delivered to the vessel 14. This prevents overtreatment and undertreatment of certain areas of the vessel 14.

Additionally, the imager 76 can be utilized for treatment planning purposes. A suitable imager 76, for example, is a sixty-four (64) element intravascular ultrasound imager, made by EndoSonics, Inc., of Rancho Cordova, Calif. which provides real time image of the vessel 14. A detailed description of a suitable imager is provided in U.S. Pat. No. 5,603,327, the contents of which is incorporated herein by reference. As illustrated in FIGS. 11B and 11C, the imager 76 includes a plurality of electrical lines 82 positioned between the delivery tube 49 and the outer structure 38 of the catheter 22.

The controller 78 typically includes a computer which is used to streamline and control the operation of the present delivery device 10. In the embodiments illustrated in FIGS. 9–11, the controller 78 can receive images from the imager 76 and determine the proper position and orientation of the attenuator section 50 in the vessel 14, as well as select the proper radiation source 30. Subsequently, the controller 78 can control the movement of radiation source 30 through the catheter 22 to the delivery section 24. During treatment, the controller 78 can monitor the orientation of the adjuster section 51, the positioning of the catheter 22, and the vital statistics of the patient 16. Upon completion of the radiation treatment, the controller 78 can remove the radiation source 30 from the delivery section 24. This allows the radiation procedure to be performed with minimal exposure to the physicians and hospital workers. Those skilled in the art will be able to design and develop the controller 78 with the teachings provided herein.

Another embodiment of the present invention is illustrated in FIGS. 12–15. In this embodiment, a single lumen, open-ended catheter 22 is utilized with an imager 76 and an adjuster section 51. The catheter 22 and the imager 76 are somewhat similar to the embodiment illustrated in FIGS. 9–11. However, in this embodiment, the adjuster section 51 is adapted to create one or more magnetic fields in the vessel 14 which modify the flow of radiation 83 from the catheter 22. Certain types of radiation, for example β rays, carry charge and can be diffused (attenuated) or focused (potentiated) with electromagnetic fields. In this embodiment, the adjuster section 51 modifies the radiation dose profile by creating one or more electromagnetic fields proximate to the radiation source 30.

Figure 13:
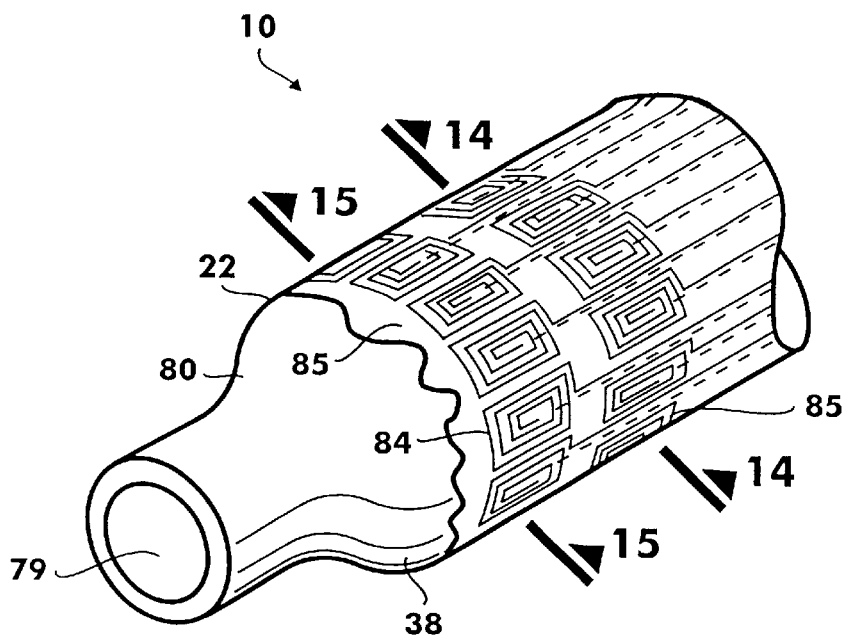
FIG. 13 is an enlarged perspective view, in partial cutaway, of a portion of the catheter of FIG. 12.

FIG. 13 illustrates a perspective view of a portion of the catheter 22. A portion of the catheter outer structure 38 is cut-away to illustrate a plurality of electrically conductive coils 84 which are impregnated into the catheter 22. The coils 84 are spaced apart and positioned around the circumference of the catheter 22. FIG. 13 illustrates two (2) sets 85 of coils 84 positioned longitudinally along the catheter 22. Each set 85 of coils 84 is positioned around the circumference of the catheter 22. The number of sets 85 of coils 84 and the number of coils 84 in each set 85 can be varied.

Electrical current applied to each of the coils 84 causes a magnetic field in each coil 84 approximately perpendicular to the plane of the respective coil 84. Depending on the direction of the current in each coil 84, the charged particle emissions passing through the coil 84 will be either attenuated or potentiated. The polarity of the magnetic field may be changed by changing the direction of the electrical current in the coil 84. The amount of particle emissions can also be modified by changing the amount of current in each coil 84. Thus, the current in each coil 84 may be independently modified to modify the radiation dose profile to suit the profile of the vessel 14. This allows for easy adjustment of the radiation dose profile in the vessel 14 without rotation of the catheter 22.

Figure 14:
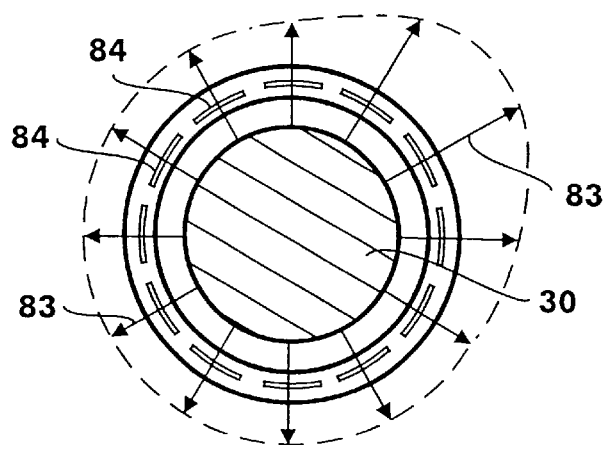
FIG. 14 is a cross-sectional schematic view which illustrates the radiation emitted from the catheter at Line 14—14 of FIG. 13.

FIG. 14 illustrates the charged particles attenuated versus the charged particles potentiated through one (1) set 85 of coils 84. Thus, the amount of radiation 83 flowing through each coil 84 can be easily adjusted. Accordingly, a substantially asymmetrical radiation dose profile relative to the radiation source 30 can be delivered to the vessel 14 by controlling the current in each of the coils 84. After imaging the vessel 14, the radiation dose profile can be modified within the vessel 14 by adjusting the current in the various coils.

Figure 15:
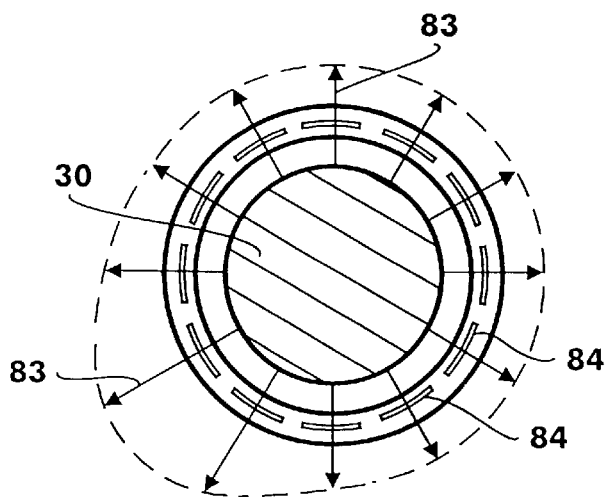
FIG. 15 is a cross-sectional schematic view which illustrates the radiation emitted from the catheter at line 15—15 of FIG. 13.

Aside from dose profile modification in the axial plane, with this embodiment, the radiation dose profile can also be adjusted longitudinally along the treatment site 12. FIG. 15 illustrates the charged particles attenuated versus the charged particles potentiated through a second set 85 of coils 84. Thus, referring to both FIGS. 14 and 15, the coils 84 in each set 85 can be adjusted so that the radiation dose profile for each set 85 of coils 84 along the longitudinal axis of the catheter 22 is different. Further, with this embodiment, there is no need to rotate the delivery device 10 because the current can be adjusted to account for different eccentrical ratios along the length of the treatment site 12.

Preferably, in this embodiment illustrated in FIGS. 12–15, the controller 78 is used to streamline and/or precisely control the dose delivery. The controller 78 assists in treatment planning and allows for the merging of the imaging of the vessel 14 with the treatment of the vessel 14. With substantially real time treatment planning, the dose prescription accuracy will be improved. Further, because of the real time nature, dose calculations can be done during the procedure, without waiting until after the catheter 22 is correctly positioned. Basically, the controller 78 reviews the images produced by the imager 76 and uses this information to provide a treatment plan. From this information, the controller 78 provides, for example, a desired radiation dose profile, a desired radiation source 30, a desired time in the body, and other treatment planning. Further, the controller 78 can take the images delivered by the imager 76 and precisely control the current in the coils 84 to provide the appropriate radiation dose delivery.

Figure 16:
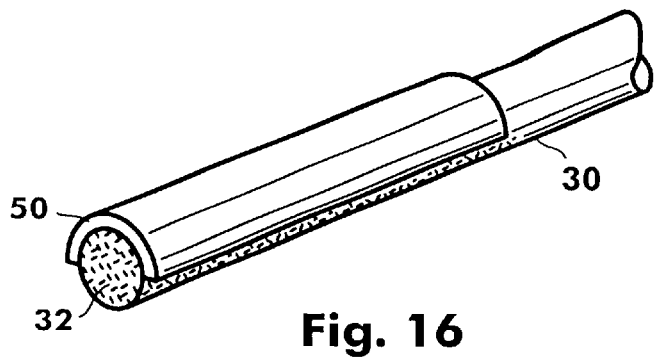
FIG. 16 is a perspective view of a radiation source having features of the present invention.
Figure 17:
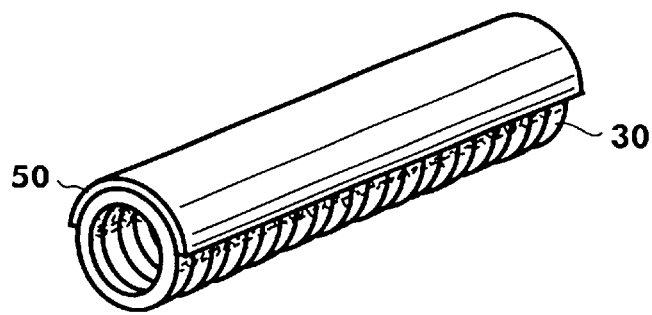
FIG. 17 is a perspective view of another embodiment of a radiation source having features of the present invention.

In yet another embodiment of the present invention, illustrated in FIGS. 16 and 17, the attenuator section 50 can be secured directly to the radiation source 30 to alter the radiation dose profile. As shown in FIG. 16, the attenuator section 50 can be an attenuator material, i.e., a foil which is wrapped around the radioactive segment 32. Alternatively, for example, the attenuator material can be adhered, i.e., by sputtering or some other method directly onto the radioactive source 30. Somewhat similar to the embodiments provided above, the size, shape, and thickness of the attenuator section 50 can be varied to vary the radiation dose profile. In this embodiment, the radioactive source 30 and attenuator section 50 can be directly inserted into the vessel 14 or can be inserted into a catheter (not shown) positioned within the vessel 14. After insertion into the vessel, the radioactive source 30 can be selectively rotated until the attenuator section 50 is closest to the vessel wall 18.

Somewhat similarly, as illustrated in FIG. 17, the radioactive source 30 can be a stent which can be positioned within the vessel 14. A more complete discussion on stents is provided in U.S. Pat. No. 5,735,872, the contents of which are incorporated herein by reference. In this embodiment, the attenuator section 50 can be an attenuator material which is wrapped around the stent and/or sputtered onto a portion of the stent. Because the attenuator material is positioned around only a portion of the stent, the stent delivers an asymmetrical radiation dose profile to the vessel 14 relative to the stent. Somewhat similar to the embodiments provided above, the size, shape, and thickness of the attenuator section 50 can be varied to vary the radiation dose profile. Preferably, the stent is positioned with a balloon catheter (not shown) which includes a balloon catheter imaging system (not shown), so that the stent is properly oriented with the vessel.

Figure 18:
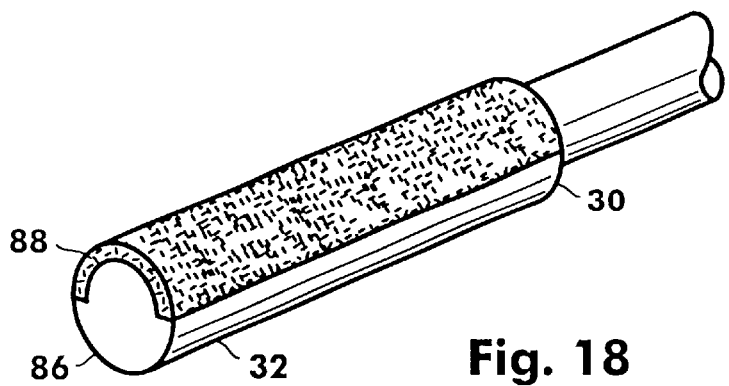
FIG. 18 is a perspective view of another embodiment of a radiation source having features of the present invention.
Figure 19:
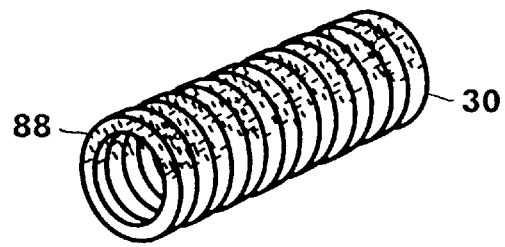
FIG. 19 is a perspective view of another embodiment of a radiation source having features of the present invention.

In still another embodiment, of the present invention as illustrated in FIGS. 18 and 19, the radiation source 30 can be manufactured to deliver an asymmetrical radiation dose profile. For example, as shown in FIG. 18, the radioactive segment 32 can include a radioactive component 88 selectively deposited or attached onto a section of a delivery wire 86. In this embodiment, the delivery wire 86, for example, can be made of titanium (Ti) and the radioactive component 88 can be made of rhenium (Re). Titanium (Ti) has a much shorter half-life than rhenium (Re). After radioactive energizing, the titanium delivery wire 86 will quickly decay when compared to the rhenium radioactive component 88. Thus, the radiation source 30 will emit a substantially asymmetrical radiation dose profile relative to the radiation source 30.

Somewhat similarly, as illustrated in FIG. 19, a stent can be caused to delivery a substantially asymmetrical radiation dose profile to the vessel wall 18. For example, a stainless steel stent can be manufactured. Subsequently, the radioactive component 88, i.e., rhenium (Re) can be deposited or applied to only a portion of the stent. Upon activation, the stent with a partial rhenium (Re) coating will delivery a substantially asymmetrical radiation dose profile in the vessel 14.

In the embodiments illustrated in FIGS. 18 and 19, the size, shape, and thickness of the radioactive component 88 can be varied to vary the radiation dose profile. Also, in the embodiments illustrated in FIGS. 18 and 19, the radioactive component 88 may be activated prior to being attached to the delivery wire 86 or the stent. This would eliminate any activation of the delivery wire 86 or the stent. Those skilled in the art will recognize that other combinations of materials can be utilized with the teachings provided herein.

Figure 20:
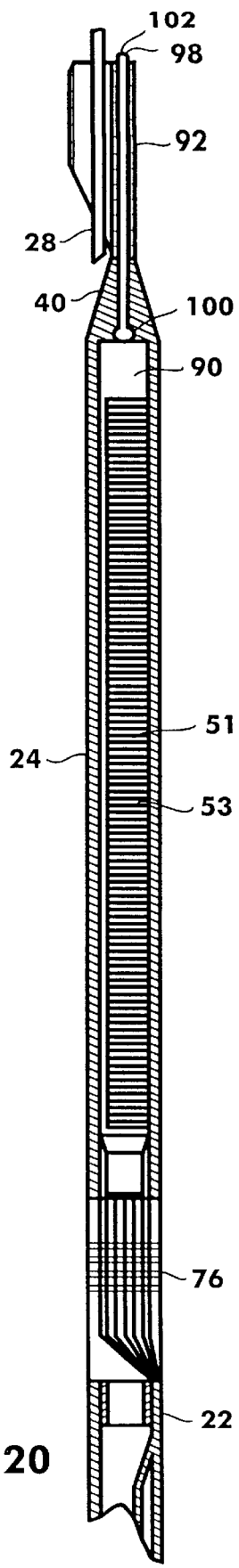
FIG. 20 is an enlarged cut-away view of a portion of another embodiment of a catheter having features of the present invention.
Figure 21:
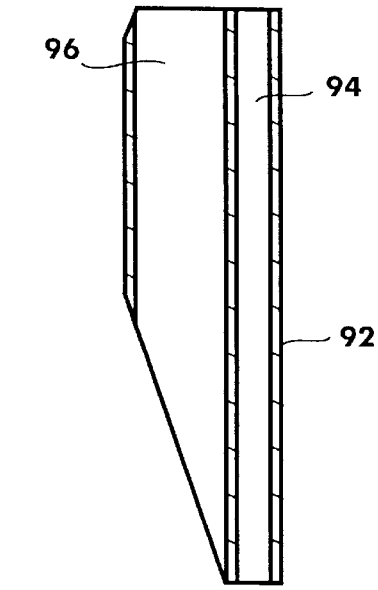
FIG. 21 is an enlarged cross-sectional view of a swivel tip of the catheter illustrated in FIG. 20.
Figure 22:
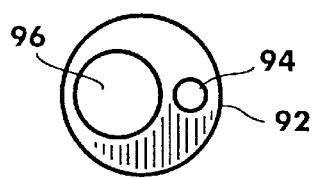
FIG. 22 is an enlarged cross-sectional view of the swivel tip of FIG. 21.

FIGS. 20–22 illustrate yet another embodiment of the present invention. This embodiment utilizes a catheter 22 having the adjuster section 51 and an imager 76. In this embodiment, the catheter 22 utilizes a single, close-ended lumen 90 which is adapted to receive the radiation source 30. The adjuster section 51 includes the plurality of adjacent semi-circular attenuator segments 53 described above. Further, the catheter supporter (not shown in FIGS. 20–22) can be integrated into the catheter outer structure 38. As provided above, the catheter outer structure 38, for example, can include a plurality of stainless steel bands which facilitate the rotation of the catheter distal end 40 to properly orient the catheter 22. Further in this embodiment, the imager 76 is built into and secured to the catheter 22. As provided above, a suitable imager 76, for example, is made by Endosonics, Inc. of Rancho Cordova, Calif.

One unique feature of the embodiment illustrated in FIG. 20, is that a swivel tip 92 is secured to the catheter distal end 40. The swivel tip 92 allows for relative rotation between the guidewire 28 and the catheter 22. As can best be seen and with reference to FIGS. 21 and 22, the swivel tip 92 is a tubular structure which includes a first swivel lumen 94 and a second swivel lumen 96. The first swivel lumen 94 is adapted to receive a swivel rod 98. The swivel rod 98 is shaped similar to a cylindrical rod and includes a spherical shaped first end 100 which is secured to the catheter distal end 40 and a spherical shaped second end 102 which retains the swivel tip 92 to the catheter 22. The swivel rod 98 allows for relative rotation between the swivel tip 92 and the catheter 22. The second swivel lumen 96 of the swivel tip 92 is adapted to receive the guidewire 28 for positioning the catheter 22 in the vessel 14.

The unique design illustrated in FIG. 20 allows for and facilitates easy rotation of the catheter 22 relative to the swivel tip 92 and the guidewire 28. Stated another way, the swivel tip 92 allows the attenuator section 50 to be easily rotated relative to the guidewire 28. Further, this facilitates the use of the single closed-ended lumen 90 with the radiation source 30 to minimize the profile of the catheter 22 and allow for the same radiation source 30 to be used for multiple patients.

OPERATION

An example of the operation of one embodiment of the device 10 can best be visualized with initial reference to FIGS. 1 and 2. First, the guiding catheter is inserted into the coronary artery ostium. Next, the guidewire 28 is positioned into the vessel 14 of the patient 16. This is done to establish a mechanical pathway through the vessel 14. Subsequently, the first imaging catheter 66 of the first imaging system 64 is inserted into the vessel lumen 36. The first imaging system 64 provides an accurate and detailed map or image of the internal structure of the vessel 14. With the information obtained from the first imaging system 64, the location of the treatment site 12, the size and shape of the vessel wall 18, and the positioning of the vessel lumen 36 relative to the vessel lamina 34 can be determined.

Next, the first imaging catheter 66 is removed and an initial vascular procedure such as angioplasty, stenting, and/or atherectomy can optionally be performed upon the vessel 14. If an initial vascular procedure is performed on the vessel 14, the first imaging catheter 66 can be reinserted into the vessel lumen 36 to provide an accurate and detailed map or image of the residual internal structure of the vessel 14. The first imaging catheter 66 is then removed from the vessel lumen 36.

Importantly, the configuration of the vessel wall 18 and the vessel 14 can be determined with information from the first imaging catheter 66. Stated another way, the residual size and shape of the vessel wall 18 and the positioning of the vessel lumen 36 relative to the vessel lamina 34 can be determined. Based upon configuration of the vessel wall 18, the configuration of the attenuator section 50, i.e., the shape, size, and thickness of the attenuator section 50 can be selected to deliver the desired radiation dose profile.

Next, the guidewire lumen 46 of the catheter 22 is moved over the guidewire 28 until the delivery section 24 is adjacent to the treatment site 12. The markers 56 on the catheter 22, proximate the delivery section 24, allow the doctor to precisely determine the location the delivery section 24 using a fluoroscope.

With the delivery section 24 adjacent the treatment site 12, the second imaging catheter 70 and the incompressible fluid are inserted into the delivery lumen 48. The second imaging system 68 provides information about the shape of the vessel wall 18 through the window section 52. With this information, the catheter proximal end 42 is rotated until the second imaging system 68 indicates when the delivery section 24 is properly oriented, i.e., the window section 52 is adjacent where the vessel lamina 34 is the farthest away. Importantly, the catheter supporter 26 transmits torque smoothly and predictably between the catheter proximal end 42 and the catheter distal end 40. This allows for the precise orientation of the window section 52, so that the window section 52 is directed at where the vessel lamina 34 is farthest away at the treatment site 12 and prevents collapse of the delivery lumen 48.

Subsequently, the catheter 22 is retained in this orientation and the second imaging catheter 70 is removed from the delivery lumen 48.

Next, the sheath 72 is installed with the dummy rod 74 into the delivery lumen 48. The dummy rod 74 is then removed and the sheath 72 remains in position within the delivery lumen 48 to protect the radiation source 30. The dummy rod 74 can be reinserted into and removed from the delivery lumen 48 a number of times to insure that the delivery lumen 48 is not collapsed and that the radioactive area 32 can be inserted into the delivery section 24 without delay.

Finally, the radioactive area 32 and the delivery wire 62 are inserted into the delivery lumen 48 until the radioactive area 32 is positioned within the delivery section 24. The radioactive area 32 remains positioned in the delivery section 32 and is allowed to emit radiation until the proposed dosage is released. Subsequently, the radiation source 30 is removed from the catheter 22 and stored in a safe container (not shown).

Another example of the operation of another embodiment of the device 10 can best be visualized with initial reference to FIGS. 9–11. In the embodiment illustrated in FIGS. 9–11, the imager 76 is built into and secured to the catheter 22. This greatly simplifies the operation of the present device 10. Because the catheter 22 includes the imager 76 built into and secured to the catheter 22, the imager 76 provides a real time image of the cross-section of the vessel 14. Based on the information from the imager 76, the attenuator section 50 can be rotated until the imager 76 indicates that the attenuator section 50 is properly oriented, i.e., window section 52 is adjacent where the vessel lamina 34 is the furthest. This allows for the precise orientation of the window section 52. Finally, the radioactive source 30 can be inserted into the delivery lumen 48, until the radioactive area 32 is positioned within the delivery section 24. The radioactive area 32 remains positioned in the delivery section 24 and is allowed to emit radiation until the proposed dosage is released. Subsequently, the radiation source 30 is removed from the catheter 22 and stored in a safe container (not shown). During treatment in this embodiment, the imager 76 can be used to constantly monitor the position of the attenuator section 50 in the vessel 14.

While the particular device 10 as herein shown and disclosed in detail is fully capable of obtaining the objects and providing the advantages herein before stated, it is to be understood that it is merely illustrative of the presently preferred embodiments of the invention. For example, the present delivery device 10 is also capable of delivering a substantially uniform dose of radiation to other areas of the vessel 14, including the vessel adventitia 35. Thus, no limitations are intended to the details of the construction or design herein shown other than as defined in the appended claims.

What is claimed is:

1. A device adapted for use with a radiation source positioned within a vessel of a patient, the device comprising an adjuster section adapted to be positioned within the vessel proximate to the radiation source, the adjuster section being adapted to alter the intensity of a portion of the radiation emitting radially from the radiation source so that the vessel receives a radiation dose profile relative to the radiation source which is substantially asymmetrical and so that two equidistant, spaced apart points relative to the radiation source on the radiation dose profile have a difference in radiation dose of between one percent and ninety-nine percent.

2. The device of claim 1 wherein the adjuster section is adapted to alter the intensity of the radiation sufficiently so that the two equidistant, points relative to the radiation source on the radiation dose profile have a difference in radiation dose of between approximately five percent and ninety percent.

3. The device of claim 1 wherein the spaced apart points are diametrically opposed and the adjuster section is adapted to alter the intensity of the radiation sufficiently so that the two spaced apart points relative to the radiation source on the radiation dose profile have a difference in radiation dose of between approximately ten percent to sixty percent.

4. The device of claim 1 wherein the adjuster section is adapted to create a magnetic field proximate to the radiation source to alter the intensity of the radiation emitting radially from the radiation source within the vessel.

5. The device of claim 1 wherein the adjuster section includes a conductor coil to alter the intensity of the radiation emitting radially from the radiation source within the vessel.

6. The device of claim 5 wherein the adjuster section includes a plurality of conductor coils which are collectively adapted to substantially encircle the radiation source within the vessel.

7. The device of claim 1 wherein the adjuster section includes an attenuator section which is adapted to attenuate a portion of the radiation emitting radially from the radiation source, the attenuator section including an attenuator material which is adapted to attenuate between one percent and ninety-nine percent of the radiation directed towards the attenuator section.

8. The device of claim 7 wherein the attenuator material is adapted to attenuate between approximately five percent and ninety percent of the radiation directed towards the attenuator section.

9. The device of clam 7 wherein the attenuator section includes a plurality of adjacent attenuator segments.

10. A catheter including the device of claim 1 secured thereto.

11. A radiation source including the device of claim 1 secured thereto.

12. The radiation source of claim 11 including a radioactive stent which is adapted to be positioned within the vessel.

13. The device of claim 1 including an imager secured proximate to the adjuster section, the imager being adapted to provide an image of the vessel from within the vessel when the radiation source is within the vessel.

14. The device of claim 1 including a controller adapted for providing a radiation treatment plan for at least a portion of the vessel.

15. A device for treating a vessel in a human, the device comprising a radiation source adapted to be positioned within the vessel, the radiation source emitting an asymmetrical radiation dose profile relative to the radiation source so that at least two equidistant, diametrically opposed points relative to the radiation source on the radiation dose profile have a difference in radiation dose of between one percent and ninety-nine percent.

16. The device of claim 15 wherein the two equidistant, diametrically opposed points relative to the radiation source on the radiation dose profile have a difference in radiation dose of between approximately five percent and ninety percent.

17. The device of claim 15 wherein the radiation source is a stent.

18. A method for delivering radiation from a radiation source to a treatment site of a vessel, the vessel having a vessel lamina, the method comprising the steps of:

positioning the radiation source within the vessel; and creating a magnetic field so that the radiation source delivers a radiation dose profile in the vessel relative to the radiation source which is substantially asymmetrical.

19. The method of claim 18 wherein the step of creating a magnetic field includes creating a magnetic field within the vessel.

20. The method of claim 18 comprising the step of imaging the vessel to determine a required strength of the magnetic field.

21. The method of claim 18 comprising the step of imaging the vessel from within the vessel substantially simultaneously with the step of creating the magnetic field.

22. The method of claim 18 including the step of adjusting the magnetic field to alter the radiation dose profile.

23. The method of claim 18 comprising the step of causing the radiation source to deliver a longitudinally irregular dose of radiation.

24. The method of claim 18 including the step of providing a radiation treatment plan for at least a portion of the vessel with a controller.

25. The method of claim 24 including the step of controlling the magnetic field with the controller.

26. The method of claim 18 wherein the step of creating a magnetic field includes the step of adjusting the magnetic field so that a substantially uniform dosage of radiation is delivered to the vessel lamina at a substantially tubular shaped treatment site.

27. A method for delivering radiation from a radiation source to a treatment site of a vessel, the vessel having a vessel lamina, the method comprising the steps of:

positioning the radiation source eccentrically within the vessel;

adjusting the radiation received by the vessel to deliver a substantially uniform dosage of radiation to the vessel lamina at the substantially tubular treatment site; and directing the dosage of radiation asymmetrically from the radiation source.

28. A method for delivering radiation from a radiation source to a treatment site of a vessel, the radiation source having a longitudinal axis, the method comprising the steps of:

positioning the radiation source within the vessel; and altering the radiation emitted radially from the radiation source to establish a radiation dose profile having a variable magnitude along the longitudinal axis of the radiation source to deliver a tailored dose of radiation to the treatment site in the vessel.

\* \* \* \* \*

UNITED STATES PATENT AND TRADEMARK OFFICE
CERTIFICATE OF CORRECTION

PATENT NO. : 6,309,339 B1
DATED : October 30, 2001
INVENTOR(S) : Jay P. Ciezki, Eugene J. Jung, Eric J. Lee, Emin M. Tuzcu, James D. Savage and Martin S. Weinhous It is certified that error appears in the above-identified patent and that said Letters Patent is hereby corrected as shown below:

Column 9,
Line 50, delete "55a" and insert -- 55b --

Column 18,
Line 49, delete "clam" insert -- claim --

Signed and Sealed this

Ninth Day of April, 2002

Attest:

JAMES E. ROGAN
Attesting Officer
Director of the United States Patent and Trademark Office

UNITED STATES PATENT AND TRADEMARK OFFICE
CERTIFICATE OF CORRECTION

PATENT NO.     : 6,309,339 B1
DATED          : October 30, 2001
INVENTOR(S)    : Jay P. Ciezki et al.

It is certified that error appears in the above-identified patent and that said Letters Patent is hereby corrected as shown below:

<u>Title page,</u>
Item [73], add:
-- The Cleveland Clinic Foundation, Cleveland, Ohio --

Signed and Sealed this

Fourteenth Day of January, 2003

JAMES E. ROGAN
*Director of the United States Patent and Trademark Office*